United States Patent [19]

Rinehart

[11] Patent Number: 5,035,003
[45] Date of Patent: Jul. 30, 1991

[54] LIQUID HEAT TRANSFER GLOVE

[76] Inventor: Dixie Rinehart, 60 Twining Flats, Aspen, Colo. 81611

[21] Appl. No.: 352,275

[22] Filed: May 16, 1989

[51] Int. Cl.⁵ ............................................. A41D 19/00
[52] U.S. Cl. .......................................... 2/159; 2/164
[58] Field of Search ................... 2/158, 164, 66, 159, 2/160, 161 A, 161 R, 272; 219/211; 36/2.6; 126/204, 206, 207, 208, 209, 210; 128/379, 381

[56] References Cited

U.S. PATENT DOCUMENTS

| | | | |
|---|---|---|---|
| 2,792,827 | 5/1957 | Gravin et al. | 2/159 X |
| 3,712,288 | 1/1973 | Weiss | 126/206 |
| 3,869,594 | 3/1975 | Shively | 128/381 X |
| 3,874,000 | 4/1975 | Altman | 2/158 |
| 4,087,675 | 5/1978 | Sansonetti | 219/211 |
| 4,281,418 | 8/1981 | Cieslak et al. | 126/206 X |
| 4,535,482 | 8/1985 | Spector et al. | 2/161 A X |
| 4,688,572 | 8/1987 | Hubbard et al. | 126/204 X |
| 4,727,602 | 3/1988 | Giese et al. | 2/160 X |
| 4,759,084 | 7/1988 | Madnick et al. | 2/158 |
| 4,846,176 | 7/1989 | Golden | 128/379 X |

FOREIGN PATENT DOCUMENTS 3517726 11/1986 Fed. Rep. of Germany .............. 2/2
19994 of 1899 United Kingdom .................... 36/2.6

Primary Examiner—Werner H. Schroeder
Assistant Examiner—Sara M. Current
Attorney, Agent, or Firm—Laff, Whitesel, Conte & Saret

[57] ABSTRACT

A glove or glove lining includes a bladder partially filled with a heat-transferring liquid. The bladder is contained within the glove shell and may be bonded to the glove lining. A pocket within the glove and preferably in the wrist area of glove contains an exothermic or endothermic chemical pack. The pocket and chemical pack are sufficiently close to the bladder to heat or cool the liquid in it. The heated or cool liquid is circulated from the wrist area to the fingertips area of the glove by gravity and by natural hand motions of the wearer's hand. This transfers the heat or coolness of the liquid through the bladder ultimately to the adjoining tissue of the hand.

4 Claims, 1 Drawing Sheet

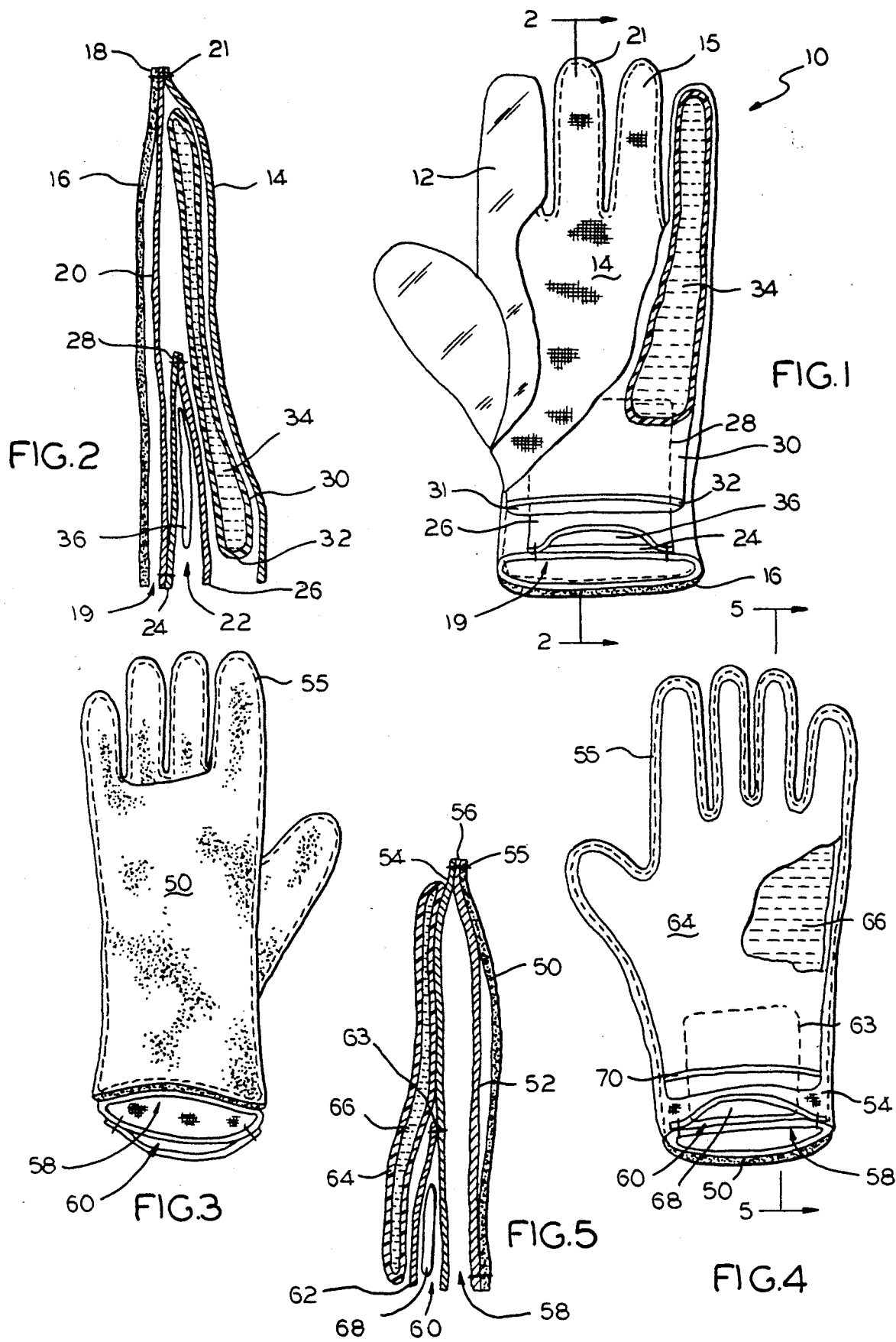

LIQUID HEAT TRANSFER GLOVE

BACKGROUND OF THE INVENTION

Protecting the hands from extreme cold or heat has been a difficult problem to solve. The hands, and particularly the fingers, are relatively small and thin extremities. As a result, they are quickly affected by ambient temperatures. The hands can be sheltered from the environment by mittens and gloves, but in either very cold or very warm environments the mittens or gloves must be thick to preserve normal or near-normal body temperature in the hands. Thick mittens or gloves, however, reduce dexterity, and extensive loss of dexterity may be unacceptable for certain activities, such as skiing, race car driving, or work in outer space.

Various means have existed for heating the palm and finger portions of the glove. In the past, electrical resistance circuits powered by batteries have been used to heat a glove. In general, prior electrical systems have been costly, unreliable and not practical due to the limited energy supply of batteries. Electrical battery operated systems do not have sufficient energy to heat the hand of the wearer for extended periods of time. Some prior heating systems for gloves have utilized exothermic packs placed within pockets on the outer surface or shell of the glove. Others have simply dropped the exothermic packs loosely into the glove. The problem with these approaches is that only that portion of the hand immediately adjacent to the pack is heated, and the heat generated is not conducted to the finger areas. Some prior systems have attempted to conduct the heat to the fingers by the use of air ducts or solid conductive materials. These prior methods do not work and are not efficient because air and solid conductive materials do not transfer enough heat from the hand area to the fingers to effectively warm the fingers in cold environments. In addition, prior methods utilizing air ducts and solid conductive materials are very bulky and restrict finger mobility and dexterity as well as being uncomfortable to the wearer.

Poor blood circulation in the hands is sometimes related to the problem of temperature regulation of the hands. Poor blood circulation tends to result in cold hands. Blood circulation can be temporarily improved by manually massaging the hands, but massage normally requires a person to stop the task he or she is doing and, if he or she is wearing gloves, to remove the gloves. This is disruptive to the task and, in very cold or very warm environments, antithetical to the purpose of wearing gloves.

SUMMARY OF THE INVENTION

The invention provides an economical, practical and simple system for heating or cooling the fingers in a glove by inserting a glove-shaped bladder partially filled with a liquid into the glove.

The liquid in the bladder is heated or cooled by placing a disposable exothermic or endothermic chemical pack in the wrist/palm area of the glove lining. The heated or cooled liquid is circulated to other areas of the hand and fingers by hand manipulation and clenching or by gravity when the hand of the wearer is positioned in a fingertips down position, thereby causing the heated or cooled liquid to move from the wrist/palm area to the fingers.

When the hand of the wearer is clasped around an object such as a tool or ski pole handle, the liquid in the bladder will be forced from the finger areas and circulated back to the bottom of the bladder in the area of the chemical packs and be reheated or cooled again. The free-flow characteristics of the liquid heat transfer medium provide for comfort and minimum restriction to dexterity and mobility of the wearer's hand during working, since the liquid will freely circulate to the wrist area during hand clasping and move out of the way of the fingers.

The glove bladder is desirably bonded to a glove lining which can be inserted into an ordinary glove shell to provide a circulating liquid heat transfer system for the purposes of heating or cooling the entire hand of the wearer. The circulating liquid in the bladder also provides a massaging action to the hand, which helps to maintain the normal temperature of the hands.

BRIEF DESCRIPTION OF THE DRAWINGS

FIG. 1 is a partial cross sectional view of a glove constructed in accordance with the invention.

FIG. 2 is a cross sectional view taken along 2—2 of FIG. 1.

FIG. 3 is a plan view of the back of an insert to a glove constructed in accordance with the invention.

FIG. 4 is a partial cross-sectional view of the front of an insert to a glove constructed in accordance with the invention.

FIG. 5 is a cross-sectional view of taken along 5—5 of FIG. 4.

DESCRIPTION OF THE PREFERRED EMBODIMENTS

A glove 10 constructed in accordance with the invention is shown in FIGS. 1 and 2. As used herein, the term "glove" is intended to include mittens as well as gloves with separately formed finger portions. The outermost layer or shell 12 of the glove 10 may be formed in any suitable manner of any suitable material, including leather, vinyl, wool, etc. Beneath the shell 12 are layers of glove lining insulation, including a palm piece 14 and a back hand piece 16. Pieces 14 and 16 include finger areas 15. These pieces may be joined together in any convenient manner, and for simplicity are shown joined together by stitching 21. The lining insulation may be composed of any comfortable material.

Beneath the glove lining insulation, on the back hand side, is a layer of innerface lining 20 made of cotton, polyester, or other suitably comfortable, open-weave fabric which freely transmits heated or cooled air (hereinafter referred to as "non-insulating material"). The innerface lining 20 is attached by stitching 21 or with an adhesive to pieces 14 and 16. A gap 19 is provided between back hand piece 16 and innerface lining 20 for insertion of the wearer's hand.

A pocket 22 is formed beneath innerface lining 20 and is preferably located in the wrist area of the glove. The pocket is formed from pocket pieces 24 and 26, which are attached together at the top and sides of the pocket as by stitching 28. The pocket pieces should be composed of a non-insulating material.

A bladder 30 is positioned between pocket piece 26 and palm piece 14, and it is desirably bonded, as with an adhesive, to the palm piece 14. The bladder is a seamless, fluid-retaining sack preferably formed with a dipped process well known in the art and composed of latex, neoprene, polyurethane, vinyl, or a similar elastic, water-tight material. Preferably, the bladder material is between two and four millimeters in thickness, so that it will not easily rupture and yet still conduct heat. The bladder 30 overlays substantially all of pocket piece 26 on one side, and on the other side extends parallel to the wearer's palm and to finger areas 15, running substantially the entire length of the fingers toward the fingertips 18 of the glove. Preferably, bladder 30 corresponds in shape to pieces 14 and 16 and is shaped generally like a rubber glove.

Inside the bladder is a liquid heat transfer medium having a freezing point substantially below 32° F. Two liquids found suitable are salt water and silicone fluid, such as Dow Type 200 fluid/50 centistoke. The typical adult-size glove will desirably contain between 3 and 4 ounces of the liquid, with a commensurately smaller amount for a child's size glove. The bladder is preferably filled with less than the maximum volume it hold so that the liquid volume can be shifted in accordance with the wearer's hand movements, as described subsequently. Bladder 30 is filled through, and then sealed at its base 31, desirably by a double heat seal 32 or a mechanical closure such as a string, rubber tie, or plastic crimp (not shown).

The liquid 34 in bladder 30 is to be heated or cooled, depending on the glove-wearer's preference, by a temperature controlling device such as an exothermic or endothermic chemical pack 36. The pack is inserted in pocket 22 as needed by the wearer. One type of suitable exothermic pack is sold by The Heat Factory, Inc. of Mission Viejo, Calif. under the trademark Heat Factory. It generally provides 6 to 12 hours of heat energy, depending upon the ambient temperature, and is disposable. Similar types of disposable chemical cooling packs are commercially available. Upon squeezing the packs, the chemicals are mixed to create an endothermic or exothermic reaction, which can be detected outside the pack.

An alternate embodiment of the invention is shown in FIGS. 3-5. This embodiment discloses a lining system for insertion into an existing lined glove shell. The glove shell itself is not shown in these Figures. In this embodiment, a foam back hand lining 50 is affixed to a back hand innerface lining 52 and to a palm side innerface lining 54. The innerface linings are composed of a non-insulating material, and pieces 50, 52, and 54 are joined as by stitching 55. A gap 58 for the insertion of the wearer's fingers is formed between lining pieces 52 and 54. A pocket 60 open at the bottom is formed by palm side innerface lining 54 and pocket piece 62, which are stitched together as at 63. The pocket piece is also non-insulating. Adjacent to the pocket 60 and extending up along the palm side innerface lining 54 substantially all the way to finger-tip area 56 is a bladder 64 constructed as described previously. The bladder contains the same type of liquid 66 as described previously. The bladder 64 is bonded to pocket piece 62 and to innerface lining piece 65 with an adhesive, and the bladder is sealed at its bottom by a double heat seal 70 or with a mechanical closure (not shown) as described for the first embodiment.

A temperature control device 68, either exothermic or endothermic, of the same types described previously, can be inserted into pocket 60.

The entire unit comprising the bladder 64, innerface lining pieces 52 and 54, foam back hand lining 50, and temperature control device 68 can be inserted into an existing lined glove shell.

In operation, the invention is simple and efficient to use. The wearer inserts a temperature control device into the pocket, either before or after putting the glove on. Exposure of the temperature control device to the air or manipulation of the wearer's fingers and hand triggers the chemical reaction in the temperature control device. The heat or cold produced by the temperature control device passes through the pocket and into the liquid in the adjoining portion of the bladder. The liquid is then heated or cooled.

Gravity and normal hand movements of the wearer circulates the heated or cooled liquid. As the liquid circulates, the warmed or cooled liquid moves from the palm area to the fingertip areas, concurrently transmitting the liquid temperature to the adjacent hand or finger tissue and warming or cooling it. When the wearer's hand is clasped around a tool or ski pole handle, for example, the liquid in the bladder is forced from the finger areas and circulates back to the palm area of the bladder adjacent to the temperature control device. The free-flow characteristic of the liquid heat transfer medium provides comfort and does not appreciably restrict the dexterity and mobility of the user's hand, since the liquid can freely circulate within the bladder to an area remote from the fingers, such as the wrist area, when finger dexterity is needed by the wearer. The free flowing liquid also tends to massage the adjacent hand tissue, which improves blood circulation and further heats the hand tissue.

The invention as described above includes a bladder positioned on the palm side of a glove, but the bladder and temperature control device could also be positioned on the back hand side of the glove by simply constructing a pocket on that side. Those who are skilled in the art will readily perceive other ways to modify the invention. Therefore, the appended claims are to be construed to cover all equivalent structures which fall within the true scope and spirit of the invention.

I claim:

1. A glove for heating or cooling the wearer's hand, said glove having a palm side and a back hand side, comprising:
    a fabric shell defining the exterior surface of said glove;
    a non-insulating lining within said shell and corresponding in shape to said shell, said lining including a pocket on the palm side of said glove;
    a bladder between said lining and said shell partially filled with a liquid on the palm side of said glove, said bladder shaped to extend parallel to substantially the entire palm side of a wearer's hand, and at least part of said bladder adjoining said pocket; and
    a non-electrical temperature control device in said pocket, said device producing the desired amount of heat energy so as to affect the temperature of said liquid in said adjoining bladder by heat transfer through said pocket in said non-insulating lining.

2. The glove of claim 1 wherein said bladder is sufficiently elastic so that said liquid is directed away from the finger area of said glove and toward said temperature control device when the wearer flexes said glove.

3. A liquid circulation assembly for controlling the temperature within a glove, said glove having an outer shell and a palm side and a back hand side, comprising:
    a non-insulating lining for impermanent insertion into an existing glove shell, said lining corresponding in shape to said glove shell, said lining including a pocket on the palm side of said glove shell;

a bladder between said lining and said shell partially filled with a liquid on the palm side of said glove, said bladder shaped to extend parallel to substantially the entire palm side of a wearer's hand, and at least part of said bladder adjoining said pocket; and a non-electrical temperature control device in said pocket, said device producing the desired amount of heat energy so as to affect the temperature of said liquid in said adjoining bladder by heat transfer through said pocket in said non-insulating lining.

4. The liquid circulation assembly of claim 3 wherein said temperature control device is a disposable chemical pack.

* * * * *